United States Patent
McKay (10) Patent No.: US 8,864,711 B2
(45) Date of Patent: Oct. 21, 2014

(54) DRUG DISPENSING BALLOON FOR TREATING DISC DISEASE OR PAIN

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/694,890

(22) Filed: Jan. 27, 2010

(65) Prior Publication Data

US 2011/0184349 A1   Jul. 28, 2011

(51) Int. Cl.
*A61M 37/00* (2006.01)

(52) U.S. Cl.
CPC ................................ *A61M 37/0069* (2013.01)
USPC ......... 604/132; 604/890.1; 604/500; 604/502

(58) Field of Classification Search
USPC .............. 604/890.1, 891.1, 6.16, 19, 21, 500, 604/502, 506, 164.01, 164.03, 272, 96.01, 604/97.01, 97.02, 103.01, 907, 915, 132; 623/11.11, 16.11, 17.11–17.12, 17.16
See application file for complete search history.

(56) References Cited

U.S. PATENT DOCUMENTS

| | | | | |
|---|---|---|---|---|
| 3,722,500 | A * | 3/1973 | Robinson | 128/830 |
| 5,411,475 | A * | 5/1995 | Atala et al. | 604/96.01 |
| 5,458,568 | A * | 10/1995 | Racchini et al. | 604/19 |
| 6,740,093 | B2 * | 5/2004 | Hochschuler et al. | 606/94 |
| 7,547,317 | B2 | 6/2009 | Cragg | |
| 7,556,650 | B2 | 7/2009 | Collins et al. | |
| 2002/0026244 | A1 | 2/2002 | Trieu | |
| 2002/0037940 | A1 * | 3/2002 | Koob et al. | 521/55 |
| 2002/0111603 | A1 * | 8/2002 | Cheikh | 604/891.1 |
| 2004/0073251 | A1 * | 4/2004 | Weber | 606/194 |
| 2004/0083002 | A1 * | 4/2004 | Belef et al. | 623/17.16 |
| 2005/0010297 | A1 * | 1/2005 | Watson et al. | 623/17.12 |
| 2005/0245938 | A1 * | 11/2005 | Kochan | 606/92 |
| 2006/0155296 | A1 * | 7/2006 | Richter | 606/94 |
| 2007/0088436 | A1 * | 4/2007 | Parsons et al. | 623/17.11 |
| 2007/0150061 | A1 * | 6/2007 | Trieu | 623/17.12 |
| 2008/0097511 | A1 * | 4/2008 | Yuan et al. | 606/192 |
| 2008/0154201 | A1 * | 6/2008 | Bates | 604/136 |
| 2009/0036799 | A1 * | 2/2009 | Sandhu et al. | 600/587 |
| 2009/0076610 | A1 | 3/2009 | Afzal | |
| 2009/0088789 | A1 | 4/2009 | ONeil et al. | |
| 2009/0171455 | A1 * | 7/2009 | Benco et al. | 623/1.49 |
| 2009/0198216 | A1 * | 8/2009 | Muni et al. | 604/514 |
| 2009/0216284 | A1 | 8/2009 | Chin et al. | |
| 2009/0254064 | A1 * | 10/2009 | Boatman | 604/509 |
| 2009/0263459 | A1 * | 10/2009 | King et al. | 424/426 |
| 2009/0275913 | A1 | 11/2009 | Trieu | |
| 2010/0137999 | A1 * | 6/2010 | Shohat | 623/23.75 |

FOREIGN PATENT DOCUMENTS

| | | |
|---|---|---|
| WO | 2007146896 A2 | 12/2007 |
| WO | 2009096822 A1 | 8/2009 |

* cited by examiner

*Primary Examiner* — Quynh-Nhu H Vu (74) *Attorney, Agent, or Firm* — Sorell Lenna & Schmidt LLP (57) ABSTRACT

Methods for administering medication at or near an intervertebral spinal disc are provided. In various embodiments, a microporous uninflated balloon is inserted into a spinal disk and after insertion of the balloon into the disc space, a medication is inserted into the interior of the balloon. Due to both the pressure on the balloon from the spine and drug diffusion, the medication moves through the pores over time.

17 Claims, 4 Drawing Sheets

DRUG DISPENSING BALLOON FOR TREATING DISC DISEASE OR PAIN

BACKGROUND

Intervertebral discs stabilize the spine and distribute forces between consecutive vertebrae. A healthy disc has two parts. First, there is an inner gelatinous nucleus pulposus. Second, there is an annulus fibrosis that surrounds, and in healthy discs, confines the nucleus pulposus.

Due to trauma, disease or aging, intervertebral discs may become damaged or displaced. For example, in some circumstances, disruption of the annulus fibrosis may allow the nucleus pulposus to protrude into a vertebral canal. This type of displacement and damage is commonly referred to as a herniated or ruptured disc, and when it occurs, the extended nucleus pulposus may press on a spinal nerve. This pressure may cause pain, numbness, nerve damage, muscle weakness and paralysis. Also, disruption of the annulus fibrosis can allow the leakage of inflammatory cytokines causing irritation and pain of surrounding nerve structures.

In other circumstances, discs deteriorate due to the normal aging process. As a disc dehydrates, the disc space height may be reduced, leading to instability of the spine, compression of nerve structures and pain.

Spinal disc pain and diseases associated with the spine may be treated by one more strategies, including but not limited to surgery physical therapy and the administration of medication.

Surgery can be an effective means by which to correct some underlying problems such as disc herniation through removal or reorientation of problematic tissue. However, surgery can be expensive, time consuming and uncomfortable. Moreover, not all patients are candidates for surgery, and surgery is not necessarily effective at treating all causes or symptoms of pain or disease.

Physical therapy alone or in combination with surgery can also be effective to treat or to alleviate some of the pain associated with different spinal conditions. However, physical therapy can be a long process and as with surgery not all patients are candidates for physical therapy.

Because neither surgery nor physical therapy alone or in combination is sufficient to treat all forms of disc disease and pain, it is important to develop better ways to administer medication to address these types of disease and pain. The current standard of care for administering medications to the back and spine is to administer biologic therapies that involve single injections of a drug solution into a disc. Unfortunately, these drug solutions are not retained in the disc for sufficient periods of time and often the drug solution remains effective only in or around the area that it treats.

SUMMARY

The methods and kits of the present invention facilitate the delivery of medications over a desired time period and desired area. Through the techniques of the present invention, one may more efficiently and more effectively administer medications to the spinal area.

In one embodiment, a method for delivering a therapeutic agent into an intervertebral disc is provided, the method comprising inserting a balloon at or near a target tissue site and injecting a medicine into the balloon, the medicine comprising an effective amount of the therapeutic agent. The balloon may be elastic and microporous and the injection of the medicine may cause the balloon to inflate.

In another embodiment, there is a method for administering medication to a spinal disc. The method comprises: inserting a balloon into a spinal disc, wherein the balloon is elastic and microporous and has an interior configured to hold a medication and an exterior configured to release the medication and is sized to fit within an intervertebral disc, and the balloon comprises a bladder having an opening to receive a medication; and inflating the balloon by depositing the medication into said balloon In another embodiment, there is a kit for treating disc pain or disease comprised of: a microporus balloon, a medicine, wherein the medicine is capable of being injected into the balloon, a needle, and a plunger.

Additional features and advantages of various embodiments will be set forth in part in the description that follows, and in part will be apparent from the description, or may be learned by the practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth herein are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

A method is provided for administering a medication to treat disc disease or pain. In the method, one inserts a balloon into a spinal disc and deposits a medication into the balloon. In some embodiments, the balloon is elastic and/or microporous.

Balloon

The balloon is an elastic substance that can be expanded by the inserted substance. The balloon is capable of holding medication and will expand as medication enters its interior. As used herein, the terms "expand" and "inflate" are used interchangeably, and refer to the change in interior volume of the balloon. The terms themselves place no limits on the substance that enters the interior of the balloon.

In some embodiments, the balloon is capable of expanding across the complete width of the nucleus pulposus of the disc and/or the complete and length of the nucleus pulposus of the disc and/or the complete and height of the nucleus pulposus of the disc. In other some embodiments, the balloon is capable of expanding across substantially all of the complete width of the nucleus pulposus of the disc and/or substantially all of the complete and length of the nucleus pulposus of the disc and/or substantially all of the complete height of the nucleus pulposus. As persons of ordinary skill in the art are aware, spinal discs are not perfect circles in their three dimensions. Additionally, the phrase "substantially all" may in some embodiments refer to at least 65%, at least 75%, at least 85%, at least 95% or at least 98% of the denoted volume or dimension.

In some embodiments, upon maximum expansion the balloon has a range in height from 1 mm to 15 mm; a range in width ranges of from 1 mm to 15 mm and a range is length of from 5 mm to 40 mm. The dimensions correspond to a volume range of between 0.004 and 7.0 cubic centimeters (ccs). In other embodiments, the height of the balloon upon expansion ranges from 3 mm to 8 mm, the width upon expansion ranges from 3 mm to 8 mm, and the length ranges from 10 mm to 30 mm. The dimensions correspond to a volume range of between 0.07 and 1.50 ccs. Examples of shapes of balloons include but are not limited to oblong, bullet-shaped, lozenge-shaped, circular, rectangular, or irregular shapes.

The balloon may be microporous. Thus, it may have a plurality of openings through which a substance that is inside the balloon can migrate out. As persons of ordinary skill in the art will readily appreciate, the rate at which a substance can migrate through the pores can be controlled in part by the size and number of pores.

In some embodiments, there are a plurality of pores, e.g., at least about 5, at least about 10, at least about 15, at least about 20, at least about 25, at lest about 30, at least about 40, at least about 50, at least about 60, at least about 80, at least about 100, or at least about 200. The pores may be regularly or irregularly distributed. Exclusive of the pores, the balloon is made of material that is impermeable or at least substantially impermeable so that no substances can migrate through its walls in those areas.

In some embodiments, the pores have an average size (with respect to the largest diameter of the pore upon maximum inflation of the balloon) of between about 0.01 micrometers and 50 micrometers or an average size of between about 0.01 micrometers and 0.1 micrometers or an average size of between about 0.1 micrometers and 1 micrometer or an average size of between about 1 micrometer and 5 micrometers, or an average size of between about 5 micrometers and 10 micrometers or an average size of between about 10 micrometers and 20 micrometers or an average size of between about 20 micrometers and 30 micrometers or an average size of between about 30 micrometers and 40 micrometers or an average size of between about 40 micrometers and 50 micrometers. In some embodiments there are no pores greater than about 60 micrometers or no pores greater than about 50 micrometers or no pores greater than about 40 micrometers or no pores greater than about 30 micrometers or no pores greater than about 20 micrometers or no pores greater than about 10 micrometers or no pores greater than about 5 micrometers or no pores greater than about 1 micrometer.

As noted above, the balloon may be made of an elastic material, and in some embodiments it may be created out of a non-degradable material. By being made of a non-degradable material, the balloon will not interfere with the disc function or cause tissue irritation as it degrades.

In some embodiments, the balloon is made out of a biocompatible material. Examples of biocompatible polymeric materials of which the balloon may be made, may comprise, consist essentially of or consist of, but are not limited to silicone, polyurethane, copolymers of silicone and polyurethane, polyolefins such as polyisobutylene and polyisoprene, neoprene, nitrile, vulvanized rubber and combinations thereof.

The balloon may be manufactured by standard processes for making balloons, and the pores may be added after manufacture of the balloon via, for example, a laser or a mechanical puncture template.

In some embodiments one balloon is inserted into a single disc. In some embodiments two or more balloons are inserted into the same disc, e.g., three, four, five or more balloons. When more than one balloon is inserted into the same disc, the balloon may contain the same or different formulations of medications. In some embodiments two (or more) balloons are inserted into different discs. For example, one balloon may be inserted in a disc above a vertebrae and another balloon may be inserted in a disc below the same vertebrae.

Prior to insertion, the balloon is in many embodiments, preferably deflated and there may be no substance within the balloon. If the balloon were not deflated prior to insertion, because the balloon has pores, any substance that were contained within the balloon would be at risk for diffusion out of the balloon prior to insertion in the disk, unless as described below other steps were taken to prevent diffusion.

In some embodiments, the balloon is either not inserted within any other structure such as a housing, or if the balloon is inserted within a housing, the housing is subsequently removed after the medicine is inserted.

Because the balloon remains in the disc without being encased in any material, the pressure on the balloon from the body forces the medicine out of the pores. The medicine will also come out of the balloon via simple diffusion as the medicine attempts to equilibrate within the disc. In some embodiments, the balloon may also be covered with a biodegradable or dissolvable coating that over time degrades or dissolves to permit the medicine to diffuse through the pores. Because the coating may be applied prior to inflation, if the appropriate amount of coating is used, the mere act of inflating will displace at least a portion of the coating and begin to permit diffusion through the pores. If an outer coating or barrier is present, the balloon may in some embodiments be partially filled prior to insertion.

The balloon is inserted into the nucleus pulposus of the disk that is the target site. One method for inserting the balloon is to use a small 10-18 gauge needle to push an uninflated balloon into the disc. The needle may push the balloon through a dilator tube, a working tube, a trocar or a cannula that has been inserted and that provides a means for accessing the disc.

The needle may also be used to push the balloon across the disk at issue. In some embodiments, the balloon is positioned across the whole disc or at least 95% of the disc, or at least 90% of the disc or at least 80% of the disc, or at least 70% of the disc or at least 60% of the disc or at least 50% of the disc. The aforementioned percentages are relative to at least one dimension, e.g., the length or the width or the height, or across two dimensions, e.g., the horizontal area defined by the length and the width of the discs.

The balloon may be pushed out of the needle with a plunger as the needle is slowly retracted. After the balloon is fully deployed, the same or a different needle may be used to fill the balloon with the medication. It may be advantageous to use the same needle because it is already in place to insert the medicament and reduces the potential discomfort to the patient by changing needles. As used herein and unless otherwise specified, the term "filled" refers to completely filling or partially filling, e.g., at least 50% of the volumetric capacity of the balloon, at least 60% of the volumetric capacity of the balloon, at least 70% of the volumetric capacity of the balloon, at least 80% of the volumetric capacity of the balloon, at least 90% of the volumetric capacity of the balloon or all of the volumetric capacity of the balloon. In some embodiments, the balloon can be filled to about 50-80% capacity or about 50-60% capacity or about 60-70% capacity or about 70-80% capacity.

Examples of ranges of pressures that may be used to insert the medicine include but are not limited to about 5-50 psi, about 5-10 psi, about 10-20 psi, about 20-30 psi, about 30-40 psi, or about 40-50 psi.

In some embodiments, the plunger that pushes the balloon out of the needle is cannulated with its tip extending into the balloon elastic bladder. After the balloon is pushed out, the medicine is injected down the cannulated plunger. After the desired amount of medicine is deposited in the balloon, the plunger is withdrawn and the elastic bladder seals itself. Finally, the needle/plunger assembly is withdrawn from the patient.

After the medication has been inserted into the balloon, the cannulated plunger can be withdrawn from an elastic bladder that seals the balloon as the elastic bladder closes shut. Finally, the needle is also withdrawn. Because the balloon contains microporosity, the balloon allows the medication to diffuse across the width of the disc over which the balloon has been placed. As the balloon reaches its fluid capacity, internal pressure will increase, creating back pressure making removal of the cannulated plunger out of the elastic bladder easy.

Figure 1A:
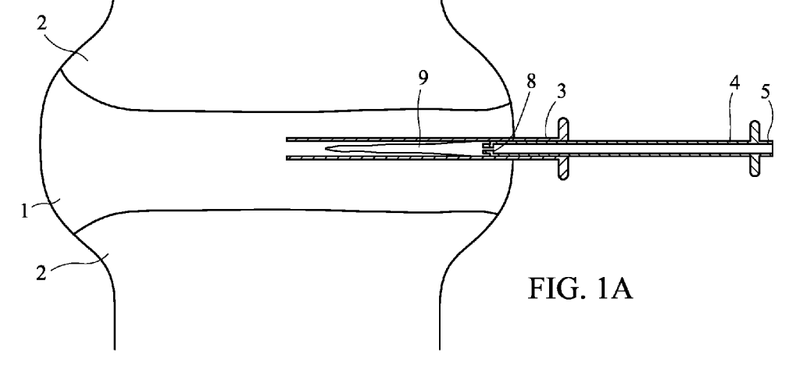
FIGS. 1A-1E represent certain steps of an embodiment of the present invention.

The invention may be further understood by reference to the accompanying figures. FIG. 1A shows an intervertebral disc 1, which is located between two vertebrae 2. A needle 3 is shown extending into the disc space. A cannulated portion of the plunger 4 is located within the needle. At one end of the plunger is a luer lock 5. The balloon 9 is shown in the lumen of the device. At the end of the plunger distal to the luer lock is a point of attachment to the seal of the balloon 8.

Figure 1B:
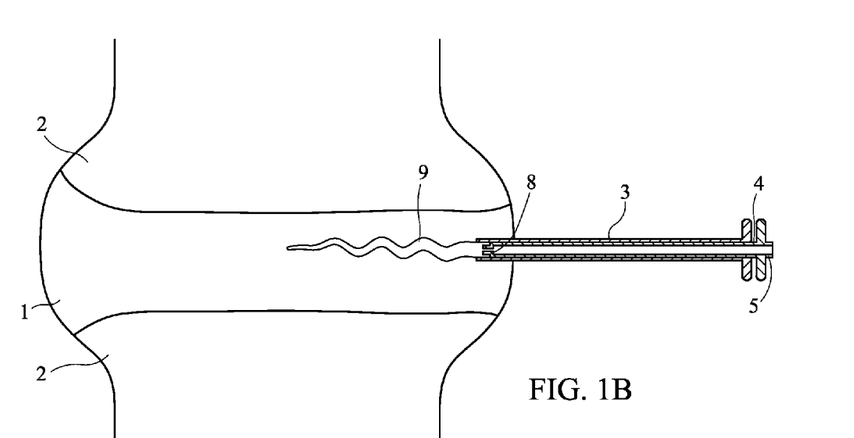

FIG. 1B shows an uninflated balloon 9 being dispensed in the disc space 1. For reference, also shown are the vertebrae 2, the tip of the plunger 8, the plunger 4 inside the device 3 and the luer lock 5.

Figure 1C:
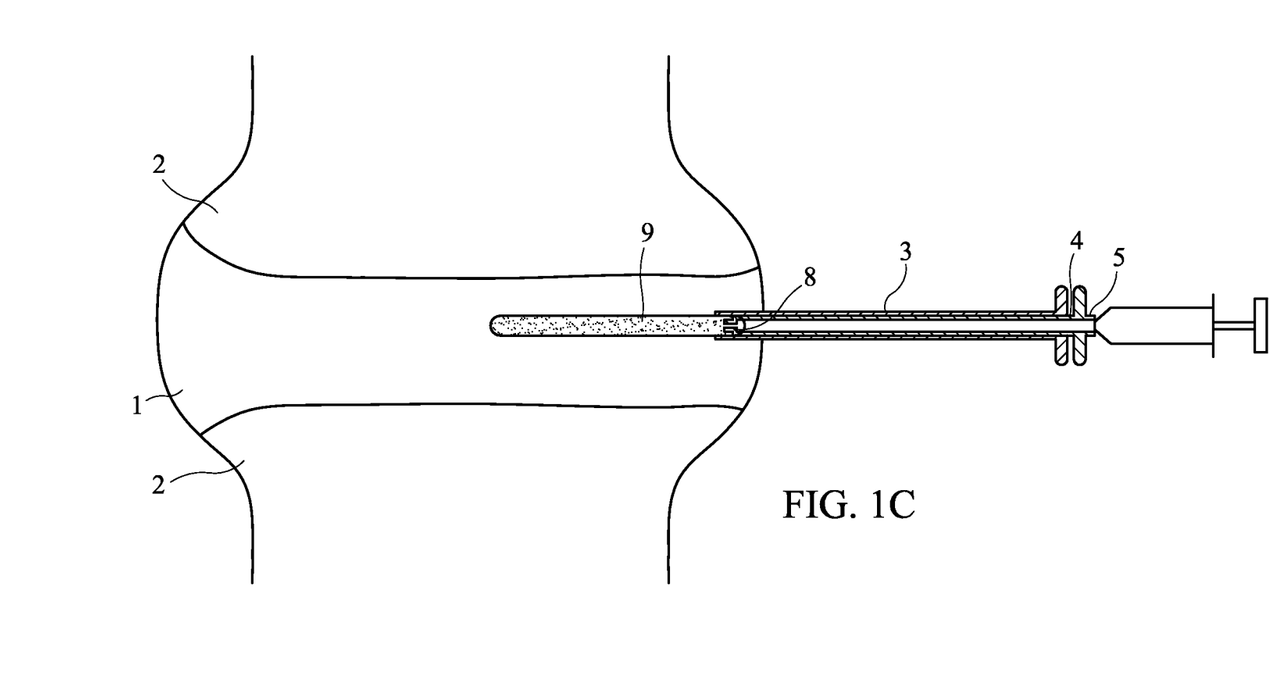

FIG. 1C shows the dispensing of the medication in the balloon 9, which is situated within the disc 1, between the vertebrae 2. The point at which the needle permits dispensing of the fluid 8 (the elastic septum of the balloon) is shown as the cannulated plunger 4 sits with the device 3 and is locked thereto at the luer lock.

Figures 1D, 1E:
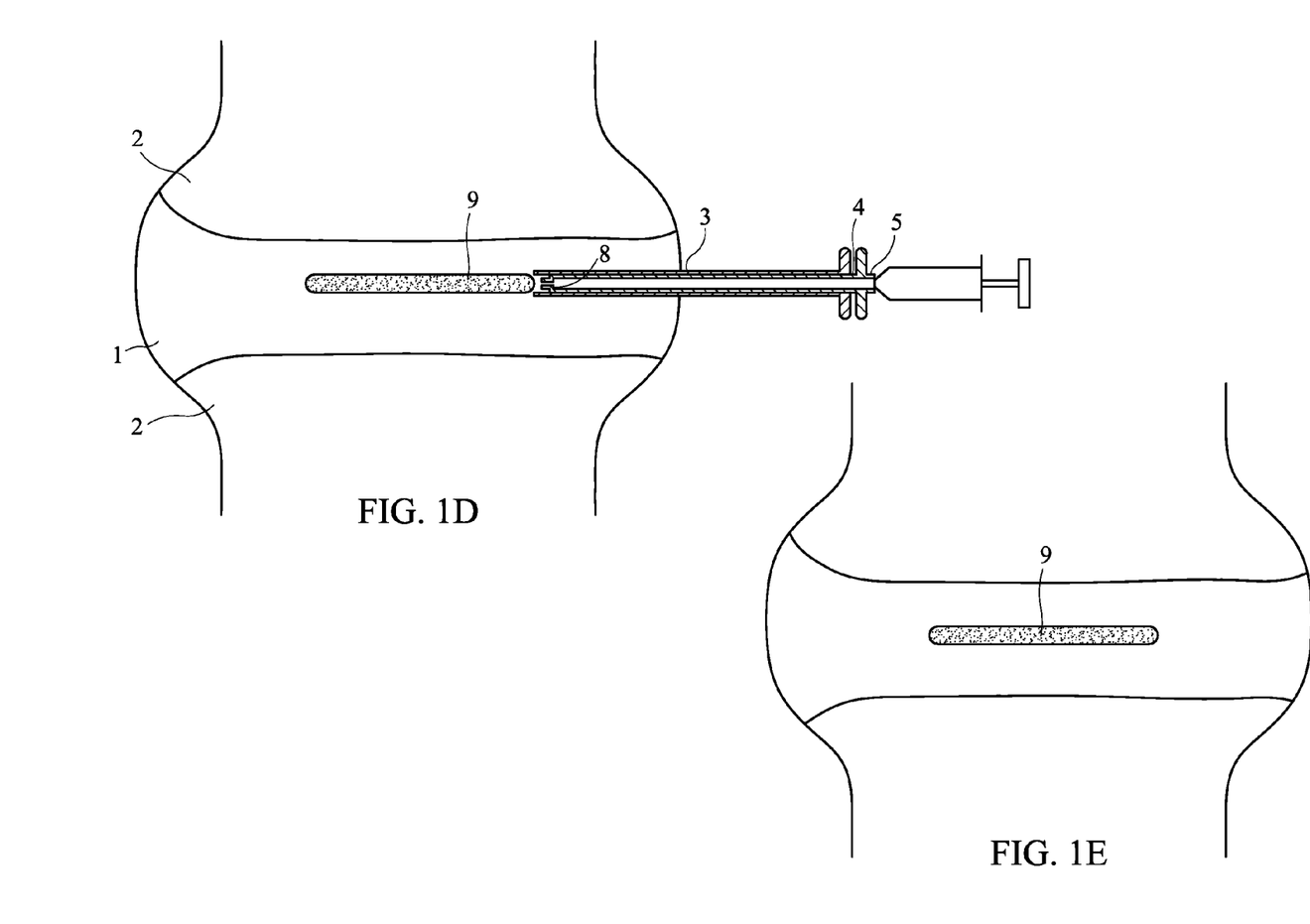

FIG. 1D shows the balloon 9 inflated balloon with the medication still attached to the needle. FIG. 1E shows the inflated microporous 9 balloon sealed in the disc.

Figure 2:
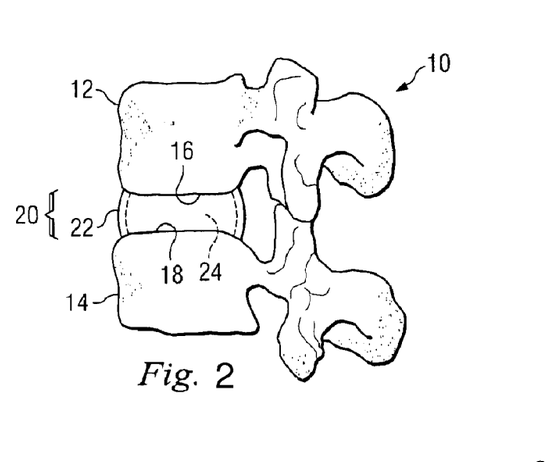
FIG. 2 represents a pair of vertebrae with a disc in which an expanded balloon is present.

FIG. 2 shows a pair of vertebrae 10. There is an upper vertebra 12 and a lower vertebrae 14, which abut the disc 22 at the upper 16 and lower 18 edge of the disc respectively. The expanded balloon 24 is shown to fill almost the entire volume of the disc. The height of the disc space is also shown 20

Figure 3:
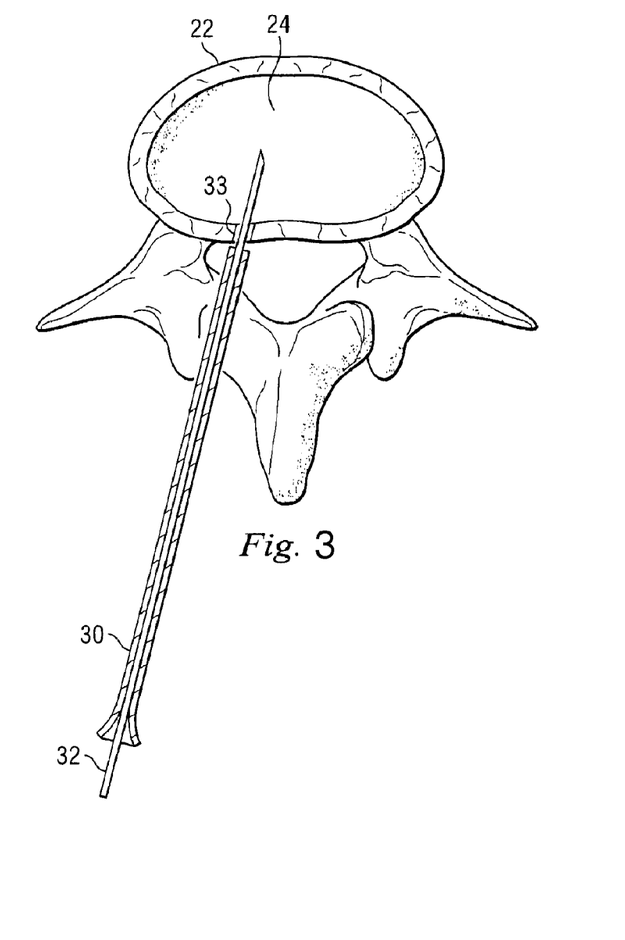
FIG. 3 represents a cross-section of a disc with a needle shown having inflated a balloon.

FIG. 3 shows a cross-section of a disc 22 with an expanded balloon 24 present. The hole in the annulus fibrosis 33 is shown. The need 32 extends through the cannula or trocar 30 into the disc. Through this needle the medication may be inserted into the balloon and cause it to expand.

Medicine and Formulations

In various embodiments, the medicine is part of a formulation. The term "medicine" as used herein is generally meant to refer to any substance that alters the physiology of a patient. The term "medicine" may be used interchangeably herein with the terms "drug," "therapeutic agent," "therapeutically effective amount," and "active pharmaceutical ingredient" or "API." It will be understood that a "medicine" formulation may include more than one therapeutic agent, wherein examples of combinations of therapeutic agents include a combination of two or more drugs. The formulation, which may, for example be a liquid, provides a concentration gradient of the therapeutic agent within the balloon for delivery to the site.

A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

Examples of amounts of the formulation to be released include but are not limited to about 1-3 ccs, or about 1-2 ccs, or about 2-3 ccs over about 4-12 weeks or about 4-6 weeks or about 6-8 weeks or about 8-10 weeks or about 10-12 weeks.

In some embodiments the formulation contains buffers or ionic solutions that may either help to increase diffusion into the disc or help to slow it down.

Examples of therapeutic agents include, those that are direct-acting and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Tres sa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, NFkb inhibitors (clonidine, sulindac), cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The formulation may contain a muscle relaxant. Examples of muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The formulation may also contain antibiotics. Examples of antibiotics that may be used, include but are not limited to nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, flerox acin, norfloxacin, ofloxacin, temafloxacin, teromyocin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

In the formulation there may also be other non-active ingredients that have a multi-functional purpose including the carrying, stabilizing and controlling the release of the therapeutic agent(s). The controlled release process, for example, may be by a solution-diffusion mechanism or it may be governed by an erosion-controlled process. Typically, the formulation will be a liquid or semi-solid formulation or a liquid having solid components dispersed throughout it comprised of a biocompatible material, which can be biodegradable. The term "solid" is intended to mean a rigid material, while, "semi-solid" is intended to mean a material that has some degree of flexibility, thereby allowing the formulation to bend and conform to the surrounding tissue requirements.

In various embodiments, the formulation may have a high drug loading, such that the therapeutic agent comprises about 5-99 wt % of the formulation, or 30-95 wt % of the formulation, or 50-95 wt % of the formulation. The balance of the formulation may include inactive materials.

The formulation may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the formulation is to be placed in the spinal area or joint area, in various embodiments, the formulation may comprise sterile preservative free material.

Radiographic markers can be included on the balloon or within the formulation to permit the user to accurately position them into the target site of the patient. These radiographic markers will also permit the user to track movement and degradation of the balloon at the site over time. In this embodiment, the user may accurately position the balloon in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. In various embodiments, the radiographic marker could be a spherical shape or a ring around the balloon.

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the balloon or formulation, or a matrix or component thereof, or as the result of metabolic transformation or dissolution of the therapeutic agent(s) or conjugates of therapeutic agent(s). Through design of the number and size of the holes, one can control the release profile of a therapeutic and cause it to be sustained release, for example, at least 2 days, at least 5 days, at least 10 days, at least 20 days, at least 30 days, at least 40 days, at least 50 days, or at least 60 days.

In various embodiments, the balloon or formulation can be designed to cause an initial burst dose of therapeutic agent within the first 24 hours after implantation. "Initial burst" or "burst effect" or "bolus dose" refers to the release of therapeutic agent from the balloon or formulation during the first 24 hours after it comes in contact with an aqueous fluid (e.g., synovial fluid, cerebral spinal fluid, etc.). The "burst effect" could be due to the increased release of therapeutic agent from the balloon while it is coagulating or hardening to form a solid or semi solid (rubbery) implant, while the medication is still in a flowable state, because of its relatively fast degradation properties, or relatively fast drug diffusion. In alternative embodiments, the balloon or formulation is designed to avoid this initial burst effect.

Inserting the Balloon

It will be appreciated by those with skill in the art that the balloon can be administered to the target site using a cannula or needle that can be a part of a drug delivery device e.g., a syringe, a gun drug delivery device, or any medical device suitable for the application of a drug to a targeted organ or anatomic region. The cannula or needle is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high nonferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle to be used, among other things, will depend on the site for implantation and the person into which it is to be implanted. For example, the width of the epidural space is only about 3-5 mm for the thoracic region and is about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the balloon implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter inbetween for insertion into a human or animal body. The widest diameter is typically about 10 gauge, while the smallest diameter is about 22 gauge. In various embodiments the gauge of the needle or cannula is about 10 to about 18 gauge or about 14 to about 16 gauge or about 16 to about 18 gauge.

In various embodiments, the cannula or needle includes dose radiographic markers that indicate location at or near the site beneath the skin, so that the user may accurately position the balloon at or near the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The medical device to administer the drug may be sterilizable. In various embodiments, one or more components of the balloon or formulation, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may also be used.

Other methods may also be used for sterilization, including, but not limited to, gas sterilization, such as, for example, with ethylene oxide or steam sterilization.

Access to the nucleus pulposus may be obtained either by cutting through the annulus if there is not already a tear or hole in the annulus, or working through an already existing opening in the annulus. Methods for accessing both an annulus and a nucleus pulposus are well-known in the art For example, access to the disc may be provided by an extraforaminal approach to the disc such as a lateral retroperitoneal approach or a paramedian approach through the paraspinal muscles. The access may be through an opening that extends through the annulus and it may have been created as a rupture in the annulus that resulted from a herniation or it may have been surgically created by an annulotomy. Access to the nucleus through an extraforaminal annulotomy may be advantageous because it does not expose the spinal canal or foramen to any undue risk. Thus, the annulus may be identified and a minimal annulotomy may be performed in order to gain access to the intradiscal space. If necessary, a curcuiate annulotmoy of up to 5 mm×5 mm may be used.

In some embodiments it may be advantageous first to insert a test balloon. A test balloon may be an uninflated or partially inflated balloon that is inserted into a disc space and then inflated to a size to which the surgeon intends to inflate the porous balloon of the present invention. The test balloon may be inflated with air or an innocuous substance (e.g., saline) so as to simulate and to provide information as to that what be a preferable size to which inflate the balloon of the present invention. If the limit on the expansion of the balloon is too great (i.e., the expanded balloon will not hold a sufficient amount of medicine), a person of ordinary skill in the art could remove additional disc material to make room for greater expansion. As persons of ordinary skill in the art will appreciate it may be advantageous to use a balloon that has no pores as the test balloon.

In some embodiments, there is a method comprising: (1) inserting a needle/plunger assembly across disc; (2) pushing a balloon out end of needle with cannulated plunger; (3) filling the balloon with medication through cannulated plunger; and (4) retracting the plunger and needle assembly from the patient.

Because the balloon is small and may be designed of materials that will not cause any adverse interaction with an organism, there is no need to remove it. Additionally, because of the small size of the balloons, it is also possible to retreat the patient with another balloon if necessary.

Kit

In various embodiments, a kit is provided that may include additional parts along with the balloon or formulation, such as medical devices that may be used to implant the balloon and to insert the medication. The kit may include the medication in a first compartment. A second compartment may include a cannulated plunger. A third compartment may include gloves, drapes, wound dressings and other procedural supplies for maintaining sterility of the implanting process, as well as an instruction booklet. A fourth compartment may include additional cannulas and/or needles. A fifth compartment may contain a microporous balloon. Each tool may be separately packaged in a plastic pouch that is radiation sterilized. A cover of the kit may include illustrations of the implanting procedure and a clear plastic cover may be placed over the compartments to maintain sterility. Further a kit may contain any two, three, or four of the aforementioned components. The kit may also come fully or partially pre-assembled.

Patients and Treatment

Patients include any biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

In various embodiments, the medication is used to treat or manage pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve, which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. The medication may also be used to halt disc degeneration or to facilitate repair.

The term "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof. Pain management medication may be administered through a microporous elastic balloon.

Another method of the present invention involves a technique similar to epidural steroid injections. The doctor (surgeon, interventional radiologist, or physiatrist) places the needle using fluoroscopic imaging and then conducts the procedure as described above. This technology may be used prior to a disc herniation. In these applications, it can be used when the annulus is still intact and only one or more partial annular tears are present.

Prior to the start of surgery, the methods of the present invention may be used to administer medications in combination with treatment of a disc herniation as follows. The injectable formulation may be pre-loaded into a syringe assembly and left on a sterile instrument table until the appropriate time for injection. The surgeon may use a traditional open or microdiscectomy technique of preference for access to the disc herniation site. Typically, the patient will be placed on a laminectomy frame in the prone position with the spine flexed to aid intraoperative exposure. The ligamemtum flavum and laminar edge are identified. A hemilaminectomy or medical facetictomy may be performed as necessary, with the aid of lateral fluoroscopy. Exposure of the hernia proceeds in a known manner, taking care to protect the dura and the nerve root. The epidural space is explored to ensure that all disc fragments have been identified.

After the disc herniation has been identified, a determination is made as to whether a further annulotomy is needed for improved access. If so, annulotomy may be performed. The herniated disc tissue may then be removed according to known techniques such as using pituitary rongeurs and/or curettes. Laminar distraction and/or flexion of the hips can be used to aid in exposure of the hernia site. In addition, distraction of the affected disc may be desired to improve the stability of the disc.

Next the balloon may be inserted on the end of a needle. After the balloon has been positioned across the disc, the needle may be retracted and a plunger may insert the formulation comprising the medication into the balloon. Through the compressive forces of the spine, the medication may be caused to exit the balloon through the pores.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for administering medication to a spinal disc, said method comprising:
    inserting a balloon into a spinal disc within a body, wherein the balloon is elastic and comprises micropores to provide sustained release of a medication comprising a therapeutic agent over at least two days, wherein the therapeutic agent comprises about 5-99 wt % of the medication and the balloon comprises an outer surface that is coated with a biodegradable or bioresorbable material, and
    inflating the balloon by depositing the medication in flowable form into said balloon, wherein the balloon is filled to about 50-80% volumetric capacity with the medication, and a needle is used to insert the balloon and the needle is positioned across the spinal disc, and the balloon is disposed within the needle and the balloon is pushed out of the needle with a plunger as the needle is retracted, whereby pressure on the balloon from the body forces the medication out of the balloon through said micropores and the medication remains in flowable form, wherein the balloon has a plurality of at least 200 micropores that upon expansion have an average size of between about 5 micrometers and 9 micrometers.

2. A method according to claim 1, wherein the needle is a 10-18 gauge needle.

3. A method according to claim 1, wherein the medication is deposited into the balloon through a needle, after the balloon is inserted into the spinal disc.

4. A method according to claim 1, wherein the medication is released over a period of about 4-12 weeks.

5. A method according to claim 1, wherein the balloon has an opening through which the medication enters the balloon and the opening seals after the needle is removed.

6. A method according to claim 1, wherein the balloon has a length that is equal to that of the disc into which it is inserted.

7. A method according to claim 1, wherein the balloon can expand to a volume of between 0.004 and 7.0 cubic centimeters.

8. A method according to claim 7, wherein the balloon can expand to a volume of between 0.07 and 1.5 cubic centimeters.

9. A method according to claim 8, wherein the balloon is made out of a biocompatible material.

10. A method according to claim 1, wherein the balloon is made out of a biocompatible material.

11. A method according to claim 1, wherein the therapeutic agent comprises about 50-95 wt % of the medication, the balance of the medication comprising inactive materials.

12. A method according to claim 1, wherein the therapeutic agent comprises an anti-inflammatory agent, analgesic agent, osteoinductive growth factor or a combination thereof.

13. A method according to claim 1, wherein at least a portion of the biodegradable or bioresorbable material coating the outer surface of the balloon is removed from the outer surface of the balloon upon inflation of the balloon.

14. A method according to claim 1, wherein the balloon is configured to release a burst dose of the medication within 24 hours after inserting the balloon into the spinal disc.

15. A method according to claim 1, wherein the plurality of micropores are irregularly distributed on the balloon.

16. A method for administering medication to a spinal disc, said method comprising:
   inserting a balloon into a spinal disc within a body, wherein the balloon is elastic and comprises micropores to provide sustained release of a medication comprising a therapeutic agent over at least two days, wherein the therapeutic agent comprises about 5-99% of the medication, the balloon has an interior configured to hold the medication and an exterior configured to release the medication and is sized to fit within an intervertebral disc, the exterior is coated with a biodegradable or bioresorbable material and the balloon comprises a bladder having an opening to receive a medication; and
   inflating the balloon by depositing the medication in flowable form into said balloon, wherein the balloon is filled to about 50-80% volumetric capacity with the medication, and a needle is used to insert the balloon and the needle is positioned across the spinal disc, and the balloon is pushed out of the needle with a plunger as the needle is retracted, whereby pressure on the balloon from the body forces medication out of the balloon through said micropores and the medication remains in flowable form wherein the balloon has a plurality of at least 200 micropores that upon expansion have an average size of between about 5 micrometers and 9 micrometers.

17. A method according to claim 16, wherein the balloon can expand to a volume of between 0.07 and 1.5 cubic centimeters.

* * * * *